US00PP12205P2

(12) United States Plant Patent
Fuess

(10) Patent No.: US PP12,205 P2
(45) Date of Patent: Nov. 20, 2001

(54) CHRYSANTHEMUM PLANT NAMED 'EMPIRE BLIZZARD'

(76) Inventor: Janet S. Fuess, 22 Country Club Dr., New York Mills, NY (US) 13417

( * ) Notice: Subject to any disclaimer, the term of this patent is extended or adjusted under 35 U.S.C. 154(b) by 0 days.

(21) Appl. No.: 09/475,972

(22) Filed: Dec. 31, 1999

(51) Int. Cl.[7] ..... A01H 5/00
(52) U.S. Cl. ..... Plt./294
(58) Field of Search ..... Plt./294

*Primary Examiner*—Howard J. Locker
(74) *Attorney, Agent, or Firm*—C. A. Whealy

(57) ABSTRACT

A distinct cultivar of Chrysanthemum plant named 'Empire Blizzard', characterized by its uniformly mounded plant habit; freely branching and large leaves; dense, full plants; uniform flowering; large flat daisy-type inflorescences that are about 6.4 cm in diameter; attractive long white ray florets that do not "pink" under low temperatures; bright yellow disc florets that develop slowly and maintain immature green coloration; numerous inflorescences per plant; and excellent garden performance.

1 Drawing Sheet

BACKGROUND OF THE INVENTION

The present invention relates to a new and distinct cultivar of Chrysanthemum plant, botanically known as *Dendranthema grandiflora* and referred to by the cultivar name Empire Blizzard.

The new cultivar is a product of a planned breeding program conducted by the Inventor in New Hartford, N.Y. The objective of the breeding program is to create new garden-type Chrysanthemum cultivars having inflorescences with desirable inflorescence forms, attractive floret colors and good garden performance.

The new cultivar originated form a cross made by the Inventor in October, 1994, of the *Dendranthema grandiflora* cultivar Empire Aspen U.S. Plant Pat. No. 7,885 as the male, or pollen, parent with an unidentified proprietary seedling selection as the female, or seed, parent.

The cultivar Empire Blizzard was discovered and selected by the Inventor as a flowering plant within the progeny of the stated cross in a controlled environment in New Hartford in September, 1995. The selection of this plant was based on its desirable inflorescence form, attractive ray floret color and excellent garden performance. Plant of new Chrysanthemum have larger inflorescences, fewer ray florets and flower more uniformly than plants of the parent cultivar, Empire Aspen.

Asexual reproduction of the new cultivar by terminal cuttings taken in a controlled environment in New Hartford has shown that the unique features of this new Chrysanthemum are stable and reproduced true to type in successive generations.

SUMMARY OF THE INVENTION

The cultivar Empire Blizzard has not been observed under all possible environmental conditions. The phenotype may vary somewhat with variations in environment such as temperature, daylength and light intensity, without, however, any variance in genotype.

The following traits have been repreatedly observed and are determined to be the unique characteristics of 'Empire Blizzard'. These characteristics in combination distinguish 'Empire Blizzard' as a new and distinct cultivar:

1. Uniformly mounded plant habit.
2. Freely branching and large leaves; dense, full plants.
3. Uniform flowering.
4. Large flat daisy-type inflorescences that are about 6.4 cm in diameter.
5. Attractive long white ray florets that do not "pink" under low temperatures.
6. Bright yellow disc florets that develop slowly and maintain immature green coloration.
7. Numerous inflorescences per plant.
8. Excellent garden performance.

The new Chrysanthemum is similar to the Chrysanthemum cultivar Tracy, disclosed in U.S. Plant Pat. No. 8,609. However in side-by-side comparisons under commercial practice, plants of the new Chrysanthemum differ from plants of the cultivar Tracy in the following characteristics:

1. Plants of the new Chrysanthemum are denser and have larger leaves than plants of the cultivar Tracy.
2. Plants of the new Chrysanthemum flower about 10 to 14 days later than plants of the cultivar Tracy under natural season conditions.
3. Plants of the new Chrysanthemum have larger inflorescences than plants of the cultivar Tracy.
4. Plants of the new Chrysanthemum have a more distinct daisy inflorescence form with fewer but longer ray florets than plants of the cultivar Tracy.
5. Plants of the new Chrysanthemum maintain green centers longer than plants of the cultivar Tracy.
6. Plants of the new Chrysanthemum flower more uniformly than plants of the cultivar Tracy.
7. Ray florets of plants of the cultivar Tracy tend to "pink" under low temperatures, whereas ray floret color of plants of the new Chrysanthemum maintain white color under low temperatures.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which more accurately describe the actual colors of the new Chrysanthemum.

The photograph at the top of the sheet comprises a top perspective view of a typical flowering plant of 'Empire Blizzard'.

The photograph at the bottom of the sheet comprises a close-up view of typical inflorescences of the cultivar 'Empire Blizzard'.

DETAILED BOTANICAL DESCRIPTION

In the following description, color references are made to The Royal Horticultural Society Colour Chart except where general terms of ordinary dictionary significance are used. The following observations and measurements describe plants grown in Pendleton, S.C., under conditions which approximate those generally used in commercial garden Chrysanthemum production. One rooted cutting was planted in a 15-cm container on Jul. 26, 1999 and plants were grown without cover under natural season conditions. Measurements and numerical values represent averages for typical flowering plants.

Botanical classification: *Dendranthema grandiflora* cultivar Empire Blizzard.

Commercial classification: Daisy-type garden chrysanthemum.

Parentage:

*Male parent.*—*Dendranthema grandiflora* cultivar Empire Aspen, disclosed in U.S. Plant Pat. No. 7,885.

*Female parent.*—Unidentified proprietary seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy-type garden Chrysanthemum. Inverted triangle; mounded plant form. Stems initially upright, then outwardly spreading giving a uniformly mounded appearance to the plant. Freely branching with lateral branches potentially developing at every node.

*Plant height.*—About 23 cm.

*Plant spread.*—About 37 cm.

*Stems.*—Texture: Pubescent. Color: 144A.

*Foliage description.*—Leaf arrangement: Alternate. Length: About 5.3 cm. Width: About 4.9 cm. Apex: Cuspidate. Base: Mostly truncate. Margin: Palmately lobed, sinuses parallel to divergent. Texture: Upper surface sparsely pubescent; lower surface moderately pubescent. Veins prominent on lower surface. Petiole length: About 1.4 cm. Petiole diameter: About 3 mm. Color: Young foliage upper surface: 147A. Young foliage lower surface: 147B. Mature foliage upper surface: 147A. Mature foliage lower surface: 147B. Venation upper surface: 147A–147B. Venation lower surface: 147B.

Inflorescence description:

*Appearance.*—Flat daisy-type inflorescence form with elongated oblong-shaped ray florets. Inflorescences borne on terminals above foliage, arising from leaf axils. Disk and ray florets arranged acropetally on a capitulum. One inflorescence per terminal with about 145 inflorescences per plant.

*Flowering response.*—Under natural season conditions, plants flower in the autumn about 80 days after planting.

*Inflorescence bud.*—Height: About 5.5 mm. Diameter: About 7.5 mm. Color: Slightly darker than 143A.

*Inflorescence size.*—Diameter: About 6.4 cm. Depth (height): About 1 cm. Diameter of disc: About 1.6 cm.

*Ray florets.*—Shape: Elongated oblong; mostly flat. Length: About 2.6 cm. Width: About 8.5 mm. Apex: Dentate. Margin: Entire. Texture: Smooth, glabrous, satiny. Orientation: Initially upright, then perpendicular to the peduncle. Number of ray florets per inflorescence: About 28. Color: When opening: White, 155D. Opened inflorescence: Upper surface: White, 155D. Lower surface: White, 155D.

*Disc florets.*—Shape: Tubular, apex dentate. Length: About 6.5 mm. Width: Apex: About 2 mm. Base: About 1 mm. Number of disc florets per inflorescence: About 159. Color: Immature: 151A. Mature: Apex: 14A. Mid-section: Whitish green. Base: White.

*Peduncle.*—Aspect: Flexible, angled about 45° to the stem. Length: First peduncle: About 6.3 cm. Third peduncle: About 7.2 cm. Diameter: About 3 mm. Texture: Pubescent. Color: Between 146A and 147A.

*Reproductive organs.*—Androecium: Present on disc florets only. Anther color: 14A. Pollen: Moderate. Pollen color: 17A. Gynoecium: Present on both ray and disc florets.

*Seed.*—Seed production has not been observed.

Disease resistance: Plants of the new Chrysanthemum have not been shown to be resistant to known Chrysanthemum diseases when grown under commercial production conditions.

It is claimed:

1. A new and distinct cultivar of Chrysanthemum plant named 'Empire Blizzard', as illustrated and described.

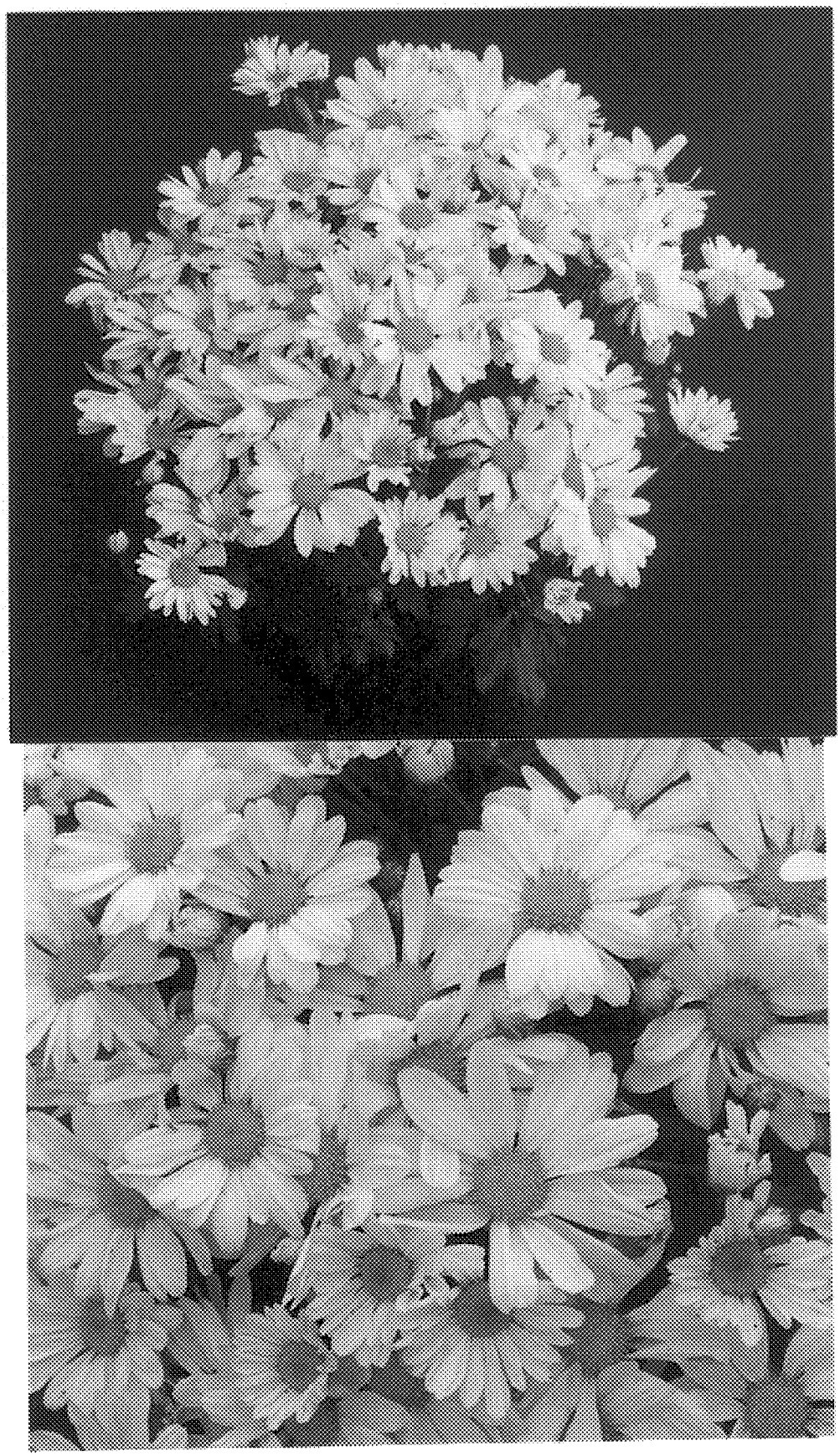

* * * * *